United States Patent
Nolan et al.

(10) Patent No.: US 11,015,796 B1
(45) Date of Patent: May 25, 2021

(54) THERMALLY DISSIPATIVE UNIBODY LIGHTING STRUCTURE

(71) Applicant: M3 Innovation, LLC, Syracuse, NY (US)

(72) Inventors: Christopher D. Nolan, Camillus, NY (US); Joseph R. Casper, Baldwinsville, NY (US)

(73) Assignee: M3 Innovation, LLC

( * ) Notice: Subject to any disclaimer, the term of this patent is extended or adjusted under 35 U.S.C. 154(b) by 0 days.

(21) Appl. No.: 16/818,220

(22) Filed: Mar. 13, 2020

Related U.S. Application Data

(60) Provisional application No. 62/940,644, filed on Nov. 26, 2019.

(51) Int. Cl.
*F21V 29/76* (2015.01)
*F21S 8/08* (2006.01)

(52) U.S. Cl.
CPC .............. *F21V 29/76* (2015.01); *F21S 8/085* (2013.01)

(58) Field of Classification Search
CPC ...... F21V 29/76; F21V 29/763; F21V 29/767; F21S 8/085; F21S 8/086
See application file for complete search history.

(56) References Cited

U.S. PATENT DOCUMENTS

| | | | | |
|---|---|---|---|---|
| 2009/0021936 A1* | 1/2009 | Stimac | ................. | F21V 23/009 362/249.02 |
| 2010/0314985 A1* | 12/2010 | Premysler | .......... | G02B 19/0061 313/46 |
| 2011/0058367 A1* | 3/2011 | Shiau | ..................... | F21V 14/02 362/218 |
| 2014/0185288 A1* | 7/2014 | Cunningham | ........ | F21V 29/717 362/235 |
| 2017/0352605 A1* | 12/2017 | Bilan | ................. | H01L 23/3672 |
| 2020/0302837 A1* | 9/2020 | Auyeung | ................ | F21V 29/83 |

* cited by examiner

*Primary Examiner* — Anabel Ton
(74) *Attorney, Agent, or Firm* — Bond Schoeneck and King PLLC; David Nocilly

(57) ABSTRACT

A self-supporting luminaire housing that can additionally support additional housings mounted for mounting to a support pole without any cross arms. The housing has a mounting plate for an illumination source, a spine spaced apart from the mounting plate, triangular fins extending between the mounting plate and the spine, and a set of braces coupled to and extending from the mounting plate to the spine. The mounting plate is rectangular, and the spine extends longitudinally relative to the mounting plate. Some of the braces extend perpendicularly from the mounting plate, and some of the braces extend obliquely from the mounting plate to form a supporting truss with the spin and the mounting plate. The housing may be formed as an integral unit to improve thermal dissipation via two thermal pathways from the illumination source to the fins.

19 Claims, 6 Drawing Sheets

THERMALLY DISSIPATIVE UNIBODY LIGHTING STRUCTURE

CROSS-REFERENCE TO RELATED APPLICATIONS

The present application claims priority to U.S. Provisional Application No. 62/940,644, filed on Nov. 26, 2019, hereby incorporated by reference in its entirety.

BACKGROUND OF THE INVENTION

1. Field of the Invention

The present invention relates to sports lighting systems and, more specifically, to a modular luminaire having a thermally dissipative housing.

2. Description of the Related Art

Conventional sports lighting systems rely on individual luminaires that are mounted to support pole. Each luminaire contains the requisite power conversion and supply electronics and is individually oriented to direct a generally circular beam of light across the area to be illuminated, such as a sporting field or similar venue. Luminaires are typically mounted to a support pole in cluster using cross-arms that are mounted to an extend laterally from the support pole to allow for a wider range of illumination, thereby requiring the use of specialized supporting structure and equipment. In addition, the lighting elements of the luminaires generate heat that must be dissipated in order to protect the components from damage or decay. Accordingly, there is the need in the art for a luminaire that can be mounted to a support pole without the need for support arms and that can provide for thermal dissipation of heat generated by the lighting elements.

BRIEF SUMMARY OF THE INVENTION

The present invention provides a luminaire housing that is self-supporting and that can additionally support additional housings mounted thereto and to a support pol without the need for cross arms. The housing comprises a mounting plate, a spine spaced apart from the mounting plate, and a plurality of fins extending between the mounting plate and the spine, and a set of braces coupled to and extending from the mounting plate to the spine. A first plurality of the set of braces extend perpendicularly from the mounting plate and are coupled to the spine and a second plurality of the set of braces extend obliquely from the mounting plate and are coupled to the spine to form a supporting truss arrangement. The plurality of fins are generally triangular and extend from a base that is coupled to the mounting plate to an apex that is coupled to the spine. The mounting plate is rectangular and extends along a plane that is parallel to a longitudinal axis of the housing. The spine extends longitudinally from the first coupler to the second coupler and may be curved. The set of braces are aligned along the mounting plate to intersect the longitudinal axis of the housing. The mounting plate, the set of braces, and the spine may be formed as an integral unit to improve thermal dissipation.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
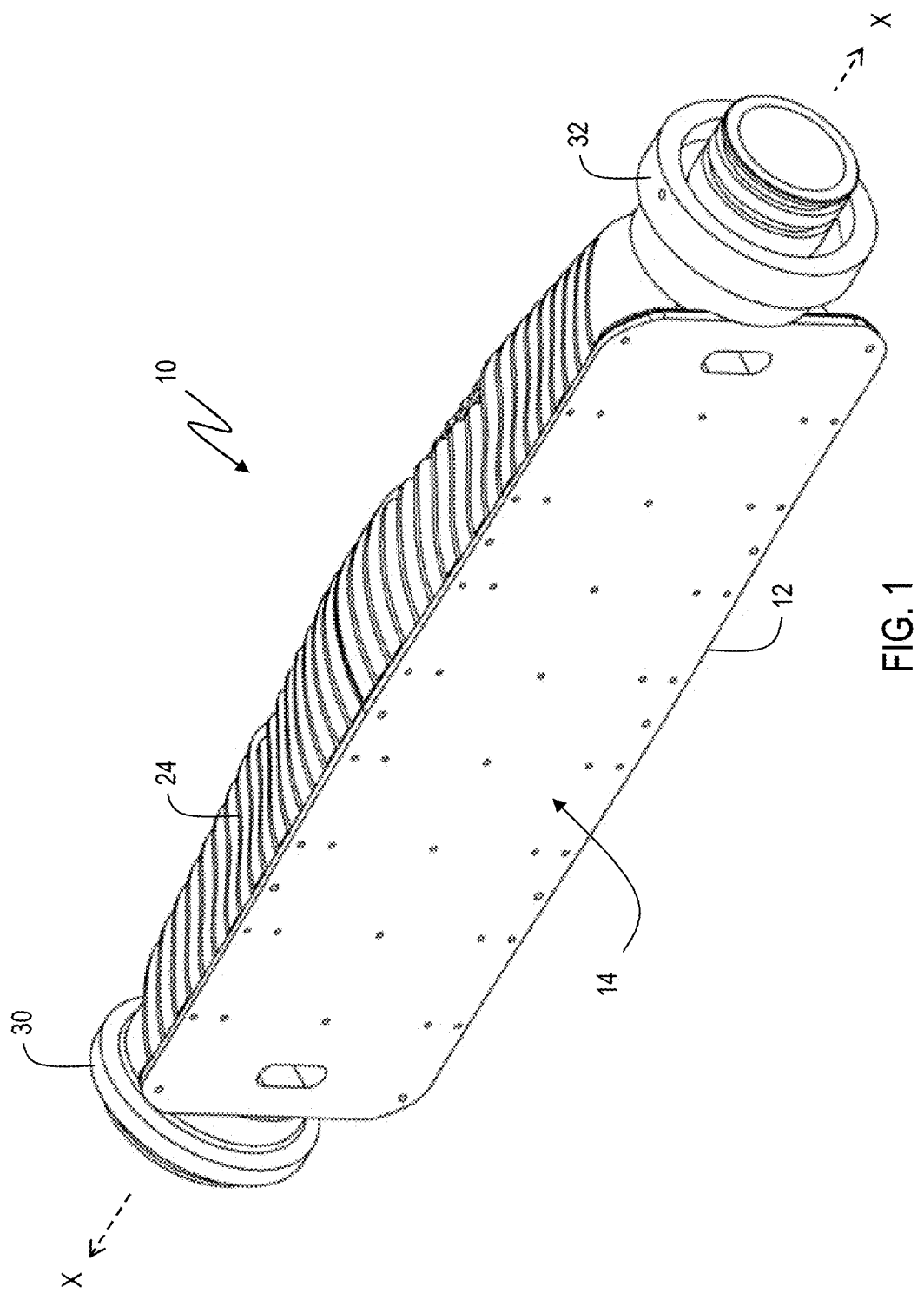
FIG. 1 is a first perspective view of a housing for a luminaire having a thermally dissipative unibody.

Referring to the figures, wherein like numerals refer to like parts throughout, there is seen in FIG. 1 a housing 10 for forming a luminaire accordingly to the present invention that has improved heat dissipation. More specifically, housing 10 extends along a longitudinal axis X-X and defines a rectangular mounting plate 12 on a front side 14 of housing 10 that defines a plane parallel to axis X-X. Mounting plate 12 is designed to support and attached to an illumination source (not shown), such as a light emitting diode array. As is known in the art, powering of the illumination source generate heat that can damage the illumination source components as well as the associated circuitry. Housing 10 is configured to act as a heat sink to remove excess heat from mounting plate 12 and then dissipate the heat into the surrounding environment. While a molded lens array may be positioned over illumination source to reduce harshness and provide sealing of the illumination source within housing 10, the rest of housing 10 is otherwise exposed to the environment for the dissipation of heat. As a result, housing 10 is preferably manufacturing from materials having useful thermal conductivity values for acting as a heat sink, such as aluminum and aluminum alloys. Housing 10, or various subparts thereof, may also be formed as an integral unit to encourage the distribution of heat therethrough, as explained in detail below.

Figure 2:
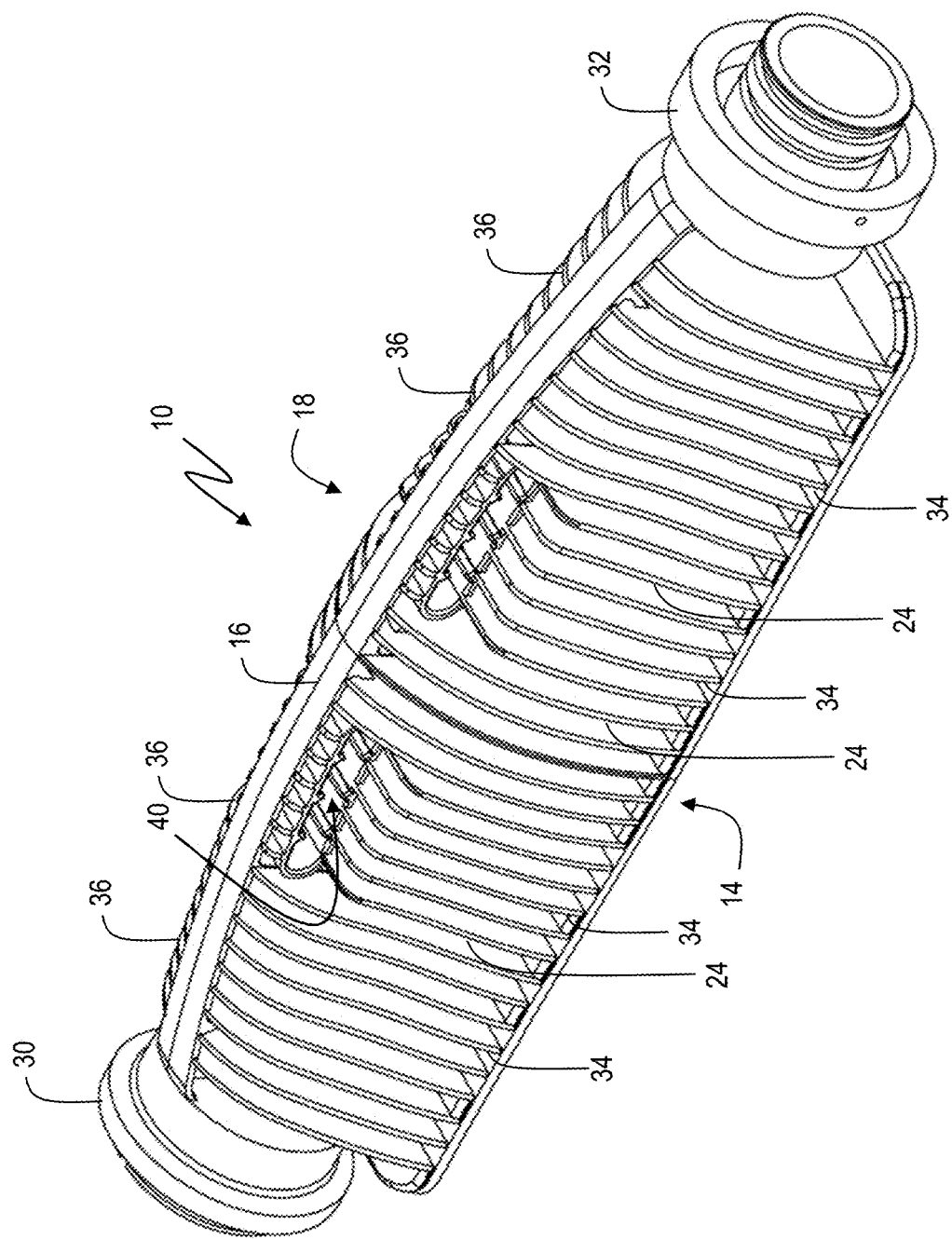
FIG. 2 is a second perspective view of a housing for a luminaire having a thermally dissipative unibody.
Figure 3:
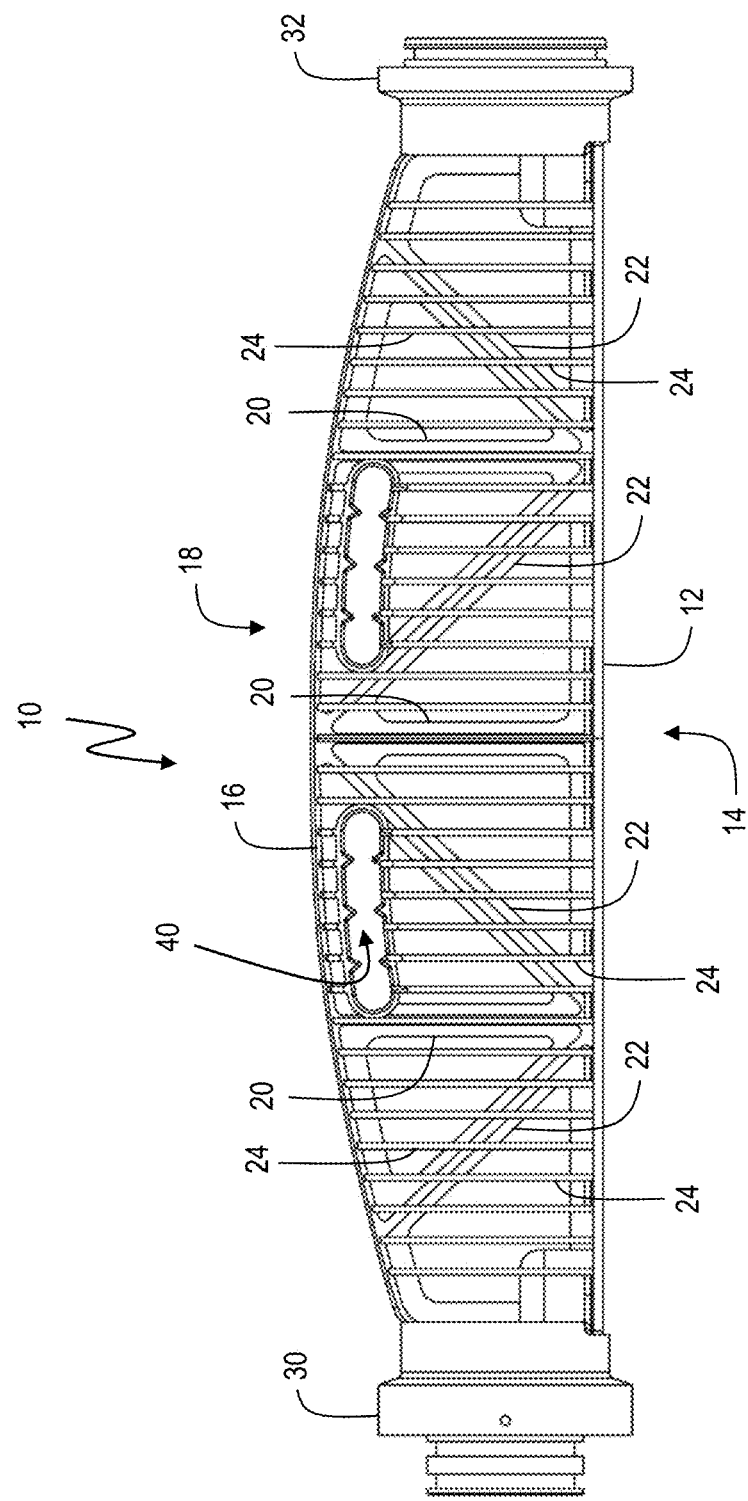
FIG. 3 is a side view of a housing for a luminaire having a thermally dissipative unibody.
Figure 4:
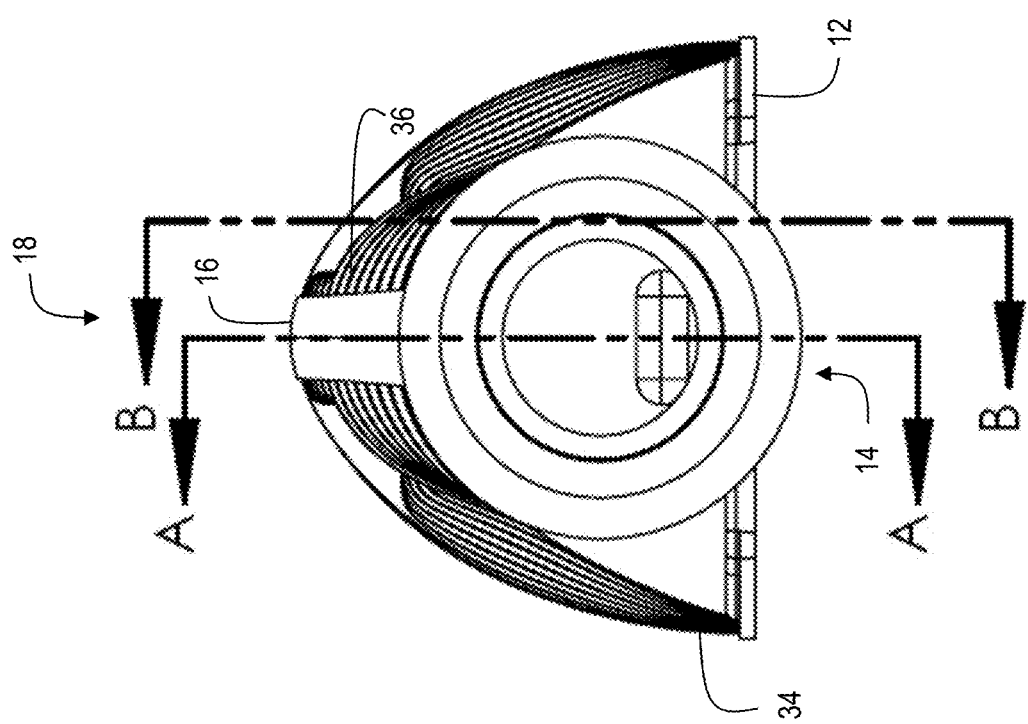
FIG. 4 is an end view of a housing for a luminaire having a thermally dissipative unibody.
Figure 5:
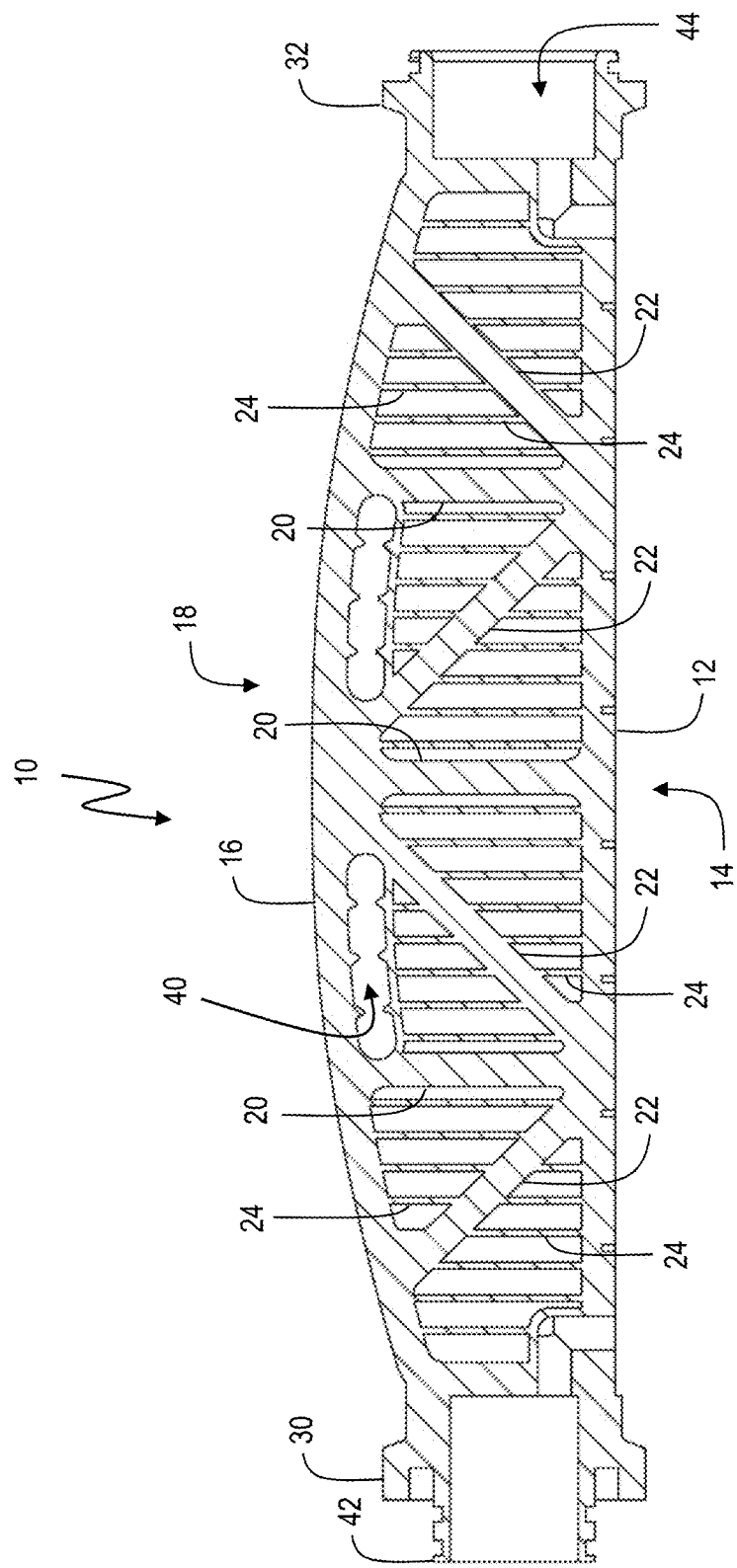
FIG. 5 is a cross-section of a housing for a luminaire having a thermally dissipative unibody taken along Line A-A of FIG. 4.

Referring to FIG. 2 through 4, housing 10 comprises a central spine 16 extending longitudinally along an opposing side of 18 housing 10 from mounting plate 12. As seen in FIG. 5, spine 16 is spaced apart from and connected to mounting plate 12 by a first plurality of braces 20 that extend orthogonally to longitudinal axis X-X and a second plurality of braces 22 that extend non-orthogonally to longitudinal axis X-X. Spine 16 is also interconnected to mounting plate 12 by a plurality of fins 24 that extend orthogonally to longitudinal axis X-X.

Figure 6:
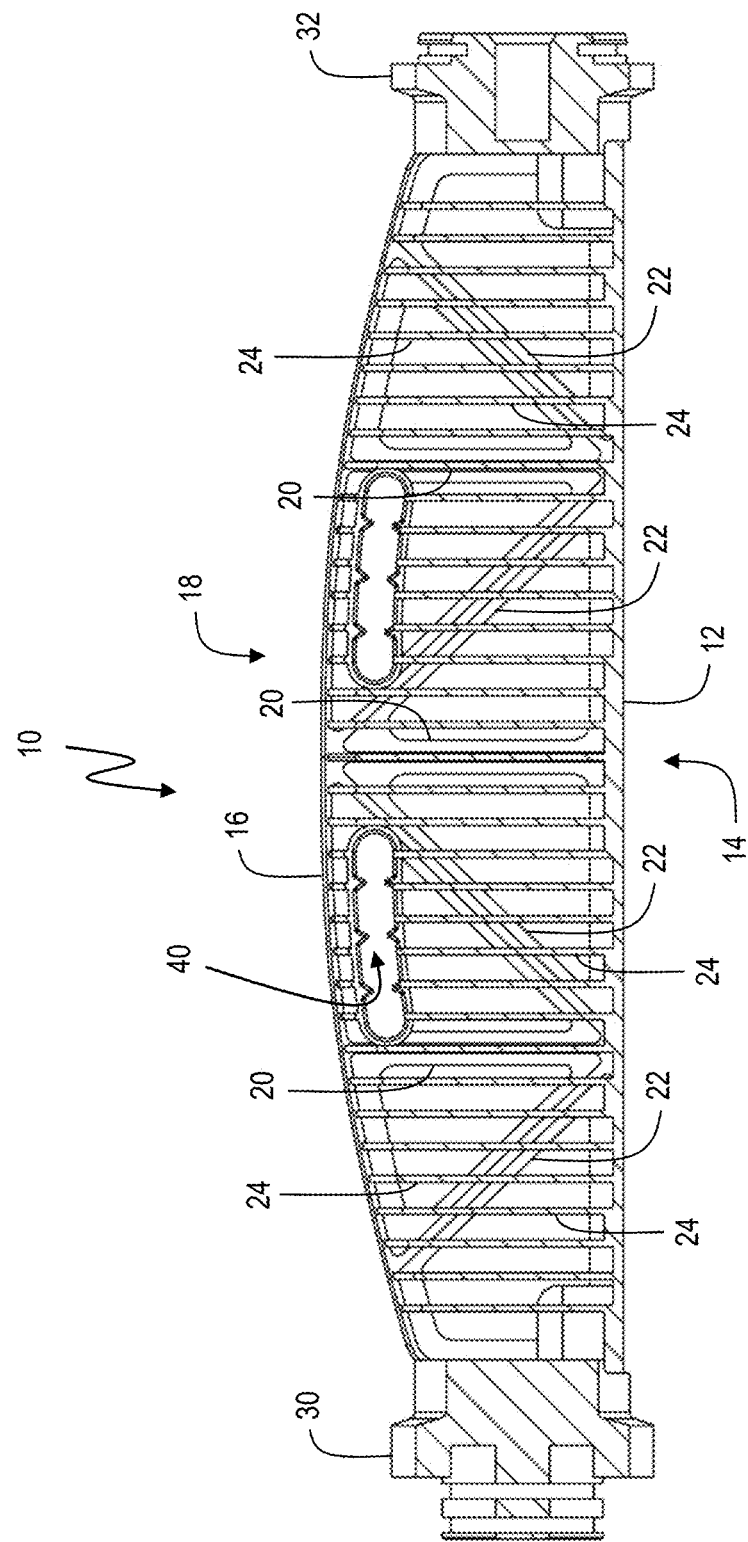
FIG. 6 is a cross-section of a housing for a luminaire having a thermally dissipative unibody taken along Line B-B of FIG. 4.

As seen in a comparison of FIG. 5 and FIG. 6, first plurality of braces 20 and second plurality of braces 22 are positioned within and confined to a central region of housing 10. First plurality of braces 20 and second plurality of braces 22 are further arranged and positioned relative to spine 16 to form a truss support for housing 10, shown in FIG. 5 as arranged similarly to a curved chord Pratt truss. Braces 20, braces 22 and spine 16 provide stability for housing 10 in all three dimensions so that housing 10 may be suspended in position, such as at the top of a pole, from either end. For example, housing 10 is seen having a pair of cylindrical couplers 30 and 32 at either end that allow housing 10 to be mounted to a support pole by one of coupler 30 and 32, with an additional housing 10 coupled to the other of couplers 30 and 32. It should be recognized that other truss or similar arrangements of spine 16, braces 20 and braces 22 may be used to provide the structural stability required for housing 10.

Fins 24 are generally triangular with a base 34 coupled to mounting plate 12 and an apex 36 coupled to spine. One or more fins 24 may have a truncated apex to define a handle opening 40 at one or more locations along housing 10 to make it easier for a user to manipulate housing 10, such as to perform a reorientation of housing 10 when mounted to a support pole, thereby changing the direction of the beam of light emitting by the illumination source coupled to mounting plate.

Housing 10 dissipates heat along two thermal pathways. First, fins 24 will directly conduct heat away from mounting plate 12 due to the direct contact between the base 34 of each fin 24 being in contact with mounting plate 12. Second, first plurality of braces 20 and second plurality of braces 22 are also in direct contact with mounting plate 12 and thus will also conduct heat away from mounting plate 12. As fins 24 are also in contact with spine 16, the heat conducted by first plurality of braces 20 and second plurality of braces 22 will flow through a second pathway to the apex 36 of fins 24. As a result, fins 24 effectively receive heat from two directions, thereby improving the thermal distribution across the surface of fins 24 and improving the thermal dissipation provided by fins 24. As noted below, the use of two thermal pathways significantly reduces the thermal gradient across fins 24, thereby significantly improves the effectiveness of fins 24 in dissipating heat generated by the illumination source.

In addition to heat dissipation, the truss arrangement of braces 20, braces 22 and spine 16 provides the structural stability for housing 10 and any additional housing 10 connected thereto. For example, as seen in FIG. 5, housing 10 includes a male interface 42 associated with coupler 30 and a female receptacle 44 at the opposing end associated with coupler 32. Two or more housings 10 may therefore be structurally jointed by inserting male interface 42 of one housing 10 into the female receptacle 44 of an adjacent housing 10 and clamped together. In this manner, several housings 10 may be interconnected together and mounted to a support pole at one end, thereby avoiding the need for support arms on the support pole as each housing 10 provides the structural stability to be self-supporting as well as supportive of additional housing 10 interconnected thereto. In addition, due to the cylindrical shape of couplers 30 and 32, each housing 10 may be rotated about its longitudinal axis to direct the illumination provided by an illumination source mounted to mounting plate 12.

Example

With respect to structural performance, in an exemplary housing 10, a total length of 26.375 inches from coupler 30 to coupler 32 may be used. Spine 16 may be configured as a "+" shaped beam with each arm of the "+" having a width of 0.188 inches and thus a total width of 0.625 inches, thereby providing a cross-sectional area of 0.2 square inches. These dimensions provide adequate stiffness for a series of four interconnected housings 10 to self-support ten times (10X) their weight. Four interconnected housings 10 will also provide an arrangement having a fundamental resonant frequency greater than 18 Hz and will be sufficiently stable to resist to hurricane velocity winds of 110 miles per hour.

With respect to thermal performance, in the exemplary housing 10 discussed above, fins 24 having a thickness of 0.125 inches may be used to provide an overall surface area of approximately 2860 square inches. The resulting surface are is sufficient for thermal dissipation of a 500 W heat flux and can maintain a temperature below 75° C. for an LED illumination array attached to mounting plate 12, which provides a surface area of about 156 inches squared. The use of two thermal pathways from mounting plate 12 to fins 24 results in a temperature gradient across fins 24 of less than about 5° C., which is a fifty percent improvement in the temperature gradient from that provided from conventional fins that are coupled only at one end to the illumination source that is generating the heat to be dissipated.

What is claimed is:

1. A luminaire housing, comprising:
   a mounting plate defining a plane:
   a spine spaced apart from the mounting plate;
   a plurality of fins extending between the mounting plate and the spine; and
   a set of braces coupled to and extending from the mounting plate to the spine, wherein a first plurality of the set of braces extend perpendicularly from the mounting plate and are coupled to the spine.

2. The luminaire housing of claim 1, wherein a second plurality of the set of braces extend obliquely from the mounting plate and are coupled to the spine.

3. The luminaire housing of claim 2, wherein the plurality of fins are triangular and have a base that is coupled to the mounting plate to define a first thermal pathway from the mounting plate to the plurality of fins.

4. The luminaire housing of claim 3, wherein the plurality of fins extent from the base to an apex that is coupled to the spine to define a second thermal pathway from the mounting plate to the plurality of fins.

5. The luminaire housing of claim 4, wherein the mounting plate is rectangular and extends along a plane that is parallel to a longitudinal axis of the luminaire housing.

6. The luminaire housing of claim 5, wherein the spine extends longitudinally from a first coupler to a second coupler.

7. The luminaire housing of claim 6, wherein the spine is curved from the first coupler to the second coupler.

8. The luminaire housing of claim 7, wherein set of braces are aligned along the mounting plate to intersect the longitudinal axis of the housing.

9. The luminaire housing of claim 8, wherein the mounting plate, the set of braces, and the spine comprise an integral unit.

10. A method of dissipating heat generated by luminaire, comprising the steps of:
    attaching an illumination source to a housing having a mounting plate defining a plane a spine spaced apart from the mounting plate, a plurality of fins extending between the mounting plate and the spine, and a set of braces coupled to and extending from the mounting plate to the spine;
    powering the illumination source to produce light and heat; and
    allowing the housing to dissipate heat from the illumination source via the mounting plate, the spine, the set of braces, and the fins.

11. The method of claim 10, wherein a first plurality of the set of braces extend perpendicularly from the mounting plate and are coupled to the spine.

12. The method of claim 10, wherein a second plurality of the set of braces extend obliquely from the mounting plate and are coupled to the spine.

13. The method of claim 12, wherein the plurality of fins are triangular and have a base that is coupled to the mounting plate to define a first thermal pathway from the mounting plate to the plurality of fins.

14. The method of claim 13, wherein the plurality of fins extend from the base to an apex that is coupled to the spine to define a second thermal pathway from the mounting plate to the plurality of fins.

15. The method of claim 14, wherein the mounting plate is rectangular and extends along a plane that is parallel to a longitudinal axis of the housing.

16. The method of claim 15, wherein the spine extends longitudinally from a first coupler to a second coupler.

17. The method of claim 16, wherein the spine is curved from the first coupler to the second coupler.

18. The method of 17, wherein the set of braces are aligned along the mounting plate to intersect the longitudinal axis of the housing.

19. The method of claim 18, wherein the mounting plate, the set of braces, and the spine comprise an integral unit.

* * * * *